United States Patent [19]

Ewen et al.

[11] Patent Number: 5,580,939
[45] Date of Patent: *Dec. 3, 1996

[54] PROCESS AND CATALYST FOR POLYOLEFIN DENSITY AND MOLECULAR WEIGHT CONTROL

[75] Inventors: John A. Ewen; Howard C. Welborn, Jr., both of Houston, Tex.

[73] Assignee: Exxon Chemical Patents Inc., Wilmington, Del.

[*] Notice: The term of this patent shall not extend beyond the expiration date of Pat. No. 5,324,800.

[21] Appl. No.: 483,920

[22] Filed: Jun. 7, 1995

Related U.S. Application Data

[60] Continuation of Ser. No. 252,487, Jun. 1, 1994, abandoned, which is a division of Ser. No. 237,464, May 3, 1994, abandoned, which is a division of Ser. No. 752,415, Aug. 30, 1991, Pat. No. 5,324,800, which is a continuation of Ser. No. 455,484, Jan. 23, 1990, abandoned, which is a continuation of Ser. No. 728,111, Apr. 29, 1995, abandoned, which is a continuation of Ser. No. 501,688, Jun. 6, 1983, abandoned.

[51] Int. Cl.$^6$ .............................. C08F 4/602; C08F 10/00
[52] U.S. Cl. ........................ 526/127; 526/150; 526/160
[58] Field of Search .................................. 526/127, 150, 526/160

[56] References Cited

U.S. PATENT DOCUMENTS

| | | | |
|---|---|---|---|
| 4,404,344 | 9/1983 | Sinn et al. | 526/160 |
| 4,530,914 | 7/1985 | Ewen et al. | 526/114 |
| 4,542,199 | 9/1985 | Kaminsky et al. | 526/348.6 |
| 4,935,474 | 6/1990 | Ewen et al. | 526/114 |
| 4,937,299 | 6/1990 | Ewen et al. | 526/114 |
| 5,324,800 | 6/1994 | Welborn et al. | 526/352 |

*Primary Examiner*—Edward J. Smith
*Attorney, Agent, or Firm*—Jaimes Sher; Myron B. Kurtzman

[57] ABSTRACT

Catalysts comprising (a) derivatives of mono, bi and tricyclopentadienyl coordination complexes with a transition metal and (b) an alumoxane are employed in a process of producing polyolefins of controlled molecular weight.

12 Claims, No Drawings

PROCESS AND CATALYST FOR POLYOLEFIN DENSITY AND MOLECULAR WEIGHT CONTROL

This is a continuation, of application Ser. No. 08/252,487 filed on Jun. 1, 1994, abandoned, which is a divisional of U.S. patent application Ser. No. 08/237,464 filed May 3, 1994, abandoned, which is a divisional of U.S. patent application Ser. No. 07/752,415 filed Aug. 30, 1991, now U.S. Pat. No. 5,324,800, which is a continuation of U.S. patent application No. 07/455,484 filed Jan. 23, 1990, now abandoned, which is a continuation of U.S. patent application Ser. No. 06/728,111 filed Apr. 29, 1985, abandoned, which is a continuation of U.S. patent application Ser. No. 06/501,688 filed Jun. 6, 1983, now abandoned.

This invention relates to an improved process for polymerizing olefins and more particularly to a method of controlling the molecular weight and/or the density of polyolefins produced so as to obtain polar product in any desired range of molecular weight and densities. The invention particularly relates to the polarization of the ethylene in the presence or absence of comonomers to polyethylenes of controlled molecular weight and density. The invention further relates to catalyst components and catalyst systems which are employed for the production of polyolefins of controlled molecular weight.

DESCRIPTION OF THE PRIOR ART

In U.S. Pat. No. 3,051,690 of Vandenberg, issued Aug. 28, 1962, there is described a process of polymerizing olefins to high molecular weight polyolefins of controlled molecular weight, as indicated by polymer viscosity, by the addition of controlled amounts of hydrogen to the polymerization system. The molecular weight control was described as useful in combination with a hydrocarbon insoluble catalyst system comprising the reaction product of a compound of a metal of Group IVB, VB, VIB and VIII with an organometallic compound of an alkali metal, alkaline earth metal, zinc, earth metal or rare earth metal. The patent teaches that increased use of hydrogen during the polymerization process results in the decrease of polymer product viscosity.

It is further known that certain metallocenes such as bis (cyclopentadienyl) titanium or zirconium dialkyls in combination with aluminum alkyl/water cocatalyst form homogeneous catalyst systems for the polymerization of ethylene.

German Patent Application 2,608,863 discloses the use of catalyst system for the polymerization of ethylene consisting of bis(cyclopentadienyl) titanium dialkyl, aluminum trialkyl and water.

German Patent Application 2,608,933 discloses an ethylene polymerization catalyst system consisting of zirconium metallocenes of the general formula $(cyclopentadienyl)_n$-$ZrY_{4-n}$, wherein n stands for a number in the range of 1 to 4, Y for R, $CH_2AlR_2$, $CH_2CH_2AlR_2$ and $CH_2CH(AlR_2)_2$, wherein R stands for alkyl or metallo alkyl, an alumiunum trialkyl cocatalyst and water.

European Patent Appln. No. 0035242 discloses a process for preparing ethylene and atactic propylene polymers in the presence of a halogen-free Ziegler catalyst system of (1) cyclopentadienyl compound of the formula $(cyclopentadienyl)_nMeY_{4-n}$ in which n is an interger from 1 to 4, Me is a transition metal, especially zirconium, and Y is either hydrogren, a $C_1$–$C_5$ alkyl or metallo alkyl group or radical having the following general formula $CH_2AlR_2$, $CH_2CH_2AlR_2$ and $CH_2CH(AlR_2)_2$ in which R represents a $C_1$–$C_5$ alkyl or metallo alkyl group, and (2) an alumoxane.

The above patents disclose that the polymerization process employing the homogeneous catalyst system is also hydrogen sensitive for molecular weight control.

An advantage of the cyclopentadienyl-metal/alumoxane catalyst system, is their extremely high activity for ethylene polymerization. Another significant advantage is that unlike olefin polymers produced in the presence of conventional heterogeneous Ziegler catalyst, terminal unsaturation is present in polymers produced in the presence of these homogeneous catalysts. The use of hydrogen for molecular weight control for these homogeneous catalysts would be disadvantageous since the terminal unsaturation would become saturated and hence, the loss of available sites for building functionalities into the olefin polymers.

In EP 352452, the patentee discloses that relatively low molecular weight polymer products are obtained at higher polymerization temperatures and relatively high molecular weight polymers at low polymerization temperatures.

As is generally known in the art, it is desirable to maximize polymerization temperatures in order to achieve high polymerization activity and reduce operating costs in terms of energy recovery. The catalyst disclosed in EP 35242 has certain disadvantages for the production of high molecular weight, high density resins since to produce such polymer products, one must operate at low temperatures thereby increasing operating costs and decreasing catalytic activity.

It would be highly desirable to provide homogeneous catalysts which can be usefully employed to produce high molecular weight polymer products at conventional polymerization temperatures and to be able to control molecular weight and density of the polymer product without resorting to temperature control or hydrogen,

SUMMARY OF THE INVENTION

Accordingly, the present invention provides new cyclopentadienyl-metal/alumoxane catalysts for olefin polymerization which catalyst can be usefully employed at high temperatures to obtain olefin polymer products having excellent properties with respect to molecular weight, density and terminal unsaturation.

It has been discovered that the molecular weight of polymer product can be controlled by the judicious selection of substituent on the cyclopentadienyl ring and use of ligands for the metallocenes. It has further been discovered that comonomer content can be controlled by the judicious selection of metallocenes. Hence, by the selection of catalyst components one can tailor polymer product with respect to molecular weight and density.

The catalysts usefully employed for the polymerization of ethylene and alpha-olefins to polyethylene homopolyolefins and copolyethylene- alpha-olefin comprise new metallocenes in combination with alumoxanes. The metallocenes employed in accordance with this invention are organometallic coordination compounds which are cyclopentadienyl derivatives of a Group 4b, 5b and 6b metal of the Periodic Table and include mono, di and tricyclopentadienyl and their derivatives of the transition metals. The metallocenes include those represented by the general formula $(C_5R'_m)_pR''_s(C_5R'_m)MeQ_{3-p}$ or $R''_s(C_5R'_m)_2MeQ'$ wherein Me is a Group 4b, 5b, or 6b metal of the Periodic Table (Chemical Rubber Company's Handbook of Chemistry & Physics, 48th edition), $(C_5R'_m)$ is a cyclopentadienyl or substituted cyclopentadienyl, each R', which can be the same or different, is hydrogen or a hydrocarbyl radical such as alkyl, alkenyl, aryl, alkylaryl, or arylalkyl radical having from 1 to 20 carbon atoms or two carbon atoms are joined together to form a $C_4$–$C_6$ ring, $R'''$ is a $C_1$–$C_4$ alkylene radical, a dialkyl germanium or silicone, or a alkyl phosphine or amine radical bridging two ($C_5R'_m$) rings, Q is a hydrocarbon radical such as aryl, alkyl, alkenyl, alkylaryl, or arylalkyl radical having from 1 to 20 carbon atoms or halogen and can be the same or different, Q' is an alkylidene radical having free 1 to about 20 carbon atoms, s is 0 or 1, p is 0, 1 or 2; when p is 0, s is 0, m is 4 when s is 1 and m is 5 when s is 0 and at least one R' is a hydrocarbyl radical when Q is an alkyl radical.

The molecular weight of the polymer product can be further controlled by the ratio of alumoxane to metallocene.

The present invention also provides a process for producing polyethylenes having a high molecular weight at relatively high temperatures. The process comprises polymerizing ethylene alone or in the presence of minor amounts of higher alpha-olefins or diolefins in the presence of the catalyst system described above.

The advantages of this invention are obtained by the use of derivatives of the cyclopentadienyl ring and/or other ligands for the metallocenes in order to control and tailor polymer molecular weight and/or comonomer content.

DETAILED DESCRIPTION OF THE INVENTION

The present invention is directed towards catalyst systems and a catalytic process for the polymerization of olefins, and particularly ethylene to high molecular weight polyethylenes such as linear low density polyethylene (LLDPE) and high density polyethylene (HDPE). The polymers are intended for fabrication into articles by extrusion, injection molding, thermoforming, rotational molding, and the like. In particular, the polymers of this invention are homopolymers of ethylene, and copolymers of ethylene with higher alpha-olefins having from 3 to about 10 carbon atoms and preferably 4 to 8 carbon atoms. Illustrative of the higher alpha-olefins are butene-1, hexene-1 and octene-1.

In the process of the present invention, ethylene, either alone or together with alpha-olefins having 3 or more carbon atoms, is polymerized in the presence of a catalyst system comprising at least one metallocene and an alumoxane.

In accordance with this invention, one can also produce olefin copolymers particularly copolymers of ethylene and higher alpha-olefins having from 3–18 carbon atoms. As indicated above, the comonomer content can be controlled through the selection of metallocene catalyst component.

The alumoxanes are polymeric aluminum compounds which can be represented by the general formulae (R—Al—O)$_n$ which is a cyclic compound and R(R—Al—O—)$_n$AlR$_2$, which is a linear compound. In the general formula R is a $C_1$–$C_5$ alkyl group such as, for example, methyl, ethyl, propyl, butyl and pentyl and n is an integer from 1 to about 20. Most preferably, R is methyl and n is about 4. Generally, in the preparation of alumoxanes from, for example, aluminum trimethyl and water, a mixture of the linear and cyclic compounds is obtained.

The alumoxane can be prepared in various ways. Preferably, they are prepared by contacting water with a solution of aluminum trialkyl, such as, for example, aluminum trimethyl, in a suitable organic solvent such as benzene or an aliphatic hydrocarbon. For example, the aluminum alkyl is treated with water in the form of a moist solvent. In an alternative method, the aluminum alkyl such as aluminum trimethyl can be desirably contacted with a hydrated salt such as hydrated copper sulfate.

Preferably, the alumoxane is prepared in the presence of a hydrated copper sulfate. The method comprises treating a dilute solution of aluminum trimethyl in, for example, toluene, with copper sulfate represented by the general formula $CuSO_4.5H_2O$. The ratio of copper sulfate to aluminum trimethyl is desirably about 1 mole of copper sulfate for 4 to 5 moles of aluminum trimethyl. The reaction is evidenced by the evolution of methane.

The new metallocene compounds usefully employed in accordance with this invention are the mono, bi and tricyclopentadienyl or substituted cyclopentadienyl metal compounds. The metallocenes are represented by the general formula $(C_5R'_m)_pR''_s(C_5R'_m)MeQ_{3-p}$ and $R''_2(C_5R'_m)_2MeQ'$ wherein ($C_5R'_m$) is a cyclopentadienyl or substituted cyclopentadienyl, each R' is the same or different and is hydrogen or a hydrocarbyl radical such as alkyl, alkenyl, aryl, alkylaryl, or arylalkyl radicals containing from 1 to 20 carbon atoms or two carbon atoms are joined together to form $C_4$–$C_6$ ring, R'' is a $C_1$–$C_4$ alkylene radical, a dialkyl germanium or silicon, or a alkyl phosphine or amine radical bridging two ($C_5R'_m$) rings, Q is a hydrocarbyl radical such as aryl, alkyl, alkenyl, alkylaryl, or arylalkyl radical having from 1–20 carbon atoms or halogen and can be the same or different, Q' is an alkylidene radical having from 1 to about 20 carbon atoms, s is 0 or 1, p is 0, 1 or 2; when p is 0, s is 0; m is 4 when s is 1 and m is 5 when s is 0, at least one R' is a hydrocarbyl radical when Q is an alkyl radical and Me is a Group 4b, 5b, or 6b metal.

Exemplary hydrocarbyl radicals are methyl, ethyl, propyl, butyl, amyl, isoamyl, hexyl, isobutyl, heptyl, octyl, nonyl, decyl, cetyl, 2-ethylhexyl, phenyl, and the like.

Exemplary alkylene radicals are methylene, ethylene, propylene, and the like.

Exemplary halogen atoms include chlorine, bromine and iodine and of these halogen atoms, chlorine is preferred.

Exemplary of the alkylidene radicals is methylidene, ethylidene and propylidene.

Of the metallocenes, zirconocenes and titanocenes are most preferred. Illustrative but non-limiting examples of these metallocenes which can be usefully employed in accordance with this invention are monocyclopentadienyls titanocenes such as, cyclopentadienyl titanium trichloride, pentamethylcyclopentadienyl titanium trichloride; bis(cyclopentadienyl) titanium diphenyl, the carbene represented by the formula $Cp_2Ti=CH_2.Al(CH_3)_2Cl$ and derivatives of this reagent such as $Cp_2TI=CH_2.Al(CH_3)_3$, $(Cp_2TiCH_2)_2$,

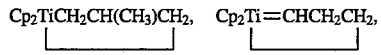

$Cp_2Ti=CH_2 .AlR'''_2Cl$, wherein Cp is a cyclopentadienyl or substituted cyclopentadienyl radical, and R''' is an alkyl, aryl or alkylaryl radical having from 1–18 carbon atoms; substituted bis(Cp)Ti(IV) compounds such as bis(indenyl)Ti diphenyl or dichloride, bis(methylcyclopentadienyl)Ti phenyl or dihalides and other dihalide complexes; dialkyl, trialkyl tetra-alkyl and penta-alkyl cyclopentadienyl titanium compounds such as bis(1,2-dimethylcyclopentadienyl)Ti diphenyl or dichloride, bis(1,2-diethylcyclopentadienyl)Ti diphenyl or dichloride and other dihalide complexes; silicone, phosphine, amine or carbon bridged cyclopentadiene complexes, such as dimethyl silyldicyclopentadienyl titanium diphenyl or dichloride, methyl phosphine dicyclopentadienyl titanium diphenyl or dichloride, methylenedicyclopentadienyl titanium diphenyl or dichloride, ethylene bis(4,5,6,7-tetrahydroindenyl)titanium dichloride and other dihalide complexes and the like.

Illustrative but non-limiting examples of the zirconocenes which can be usefully employed in accordance with this invention are, cyclopentadienyl zirconium trichloride, pentamethylcyclopentadienyl zirconium trichloride, bis(cyclopentadienyl)zirconium diphenyl, bis(cyclopentadienyl)zirconium dimethyl, the alkyl substituted cyclopentadienes, such as bis(ethyl cyclopentadienyl)zirconium dimethyl bis($\beta$-phenylpropylcyclopentadienyl)zirconium dimethyl {hereafter referred to as (B-PP-Cp)$_2$Zr dimethyl}, bis(methylcyclopentadienyl)zirconium dimethyl, and dihalide complexes of the above; di-alkyl, tri-alkyl, tetra-alkyl, and penta-alkyl cyclopentadienes, such as bis(pentamethylcyclopentadienyl)zirconium dimethyl, bis (1,2-dimethylcyclopentadienyl)zirconium dimethyl, bis(1,3-diethylcyclopentadienyl)zirconium dimethyl and dihalide complexes of the above; silicon, phosphorus, and carbon bridged cyclopentadiene complexes such as dimethylsilyldicyclopentadienyl zirconium dimethyl or dihalide, methylphosphine dicyclopentadienyl zirconium dimethyl or dihalide, and methylene dicyclopentadienyl zirconium dimethyl or dihalide, carbenes represented by the formulae Cp$_2$Zr=CH$_2$P(C$_6$H$_5$)$_2$CH$_3$, and derivatives of these compounds such as

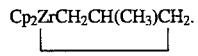

Cp$_2$ZrCH$_2$CH(CH$_3$)CH$_2$.

Bis(cyclopentadienyl)hafnium dichloride, bis(cyclopentadienyl)hafnium dimethyl, bis(cyclopentadienyl)vanadium dichloride and the like are illustrative of other metallocenes.

The ratio of aluminum in the alumoxane to total metal in the metallocenes can be in the range of about 0.5:1 to about 10,000:1, and preferably about 5:1 to about 1000:1.

The solvents used in the preparation of the catalyst system are inert hydrocarbons, in particular a hydrocarbon that is inert with respect to the catalyst system. Such solvents are well known and include, for example, isobutane, butane, pentane, hexane, heptane, octane, cyclohexane, methylcyclohexane, toluene, xylene and the like.

As a further control and refinement of polymer molecular weight, one can vary the concentration alumoxane. Higher concentrations of alumoxane in the catalyst system results in higher polymer product molecular weight.

Since, in accordance with this invention, one can produce high viscosity polymer product at relatively high temperature, temperature does not constitute a limiting parameter as with the prior art metallocene/alumoxane catalyst. The catalyst systems described herein, therefore, are suitable for the polymerization of olefins in solution, slurry or gas phase polymerizations and over a wide range of temperatures and pressures. For example, such temperatures may be in the range of about −60° C. to about 280° C. and especially in the range of about 50° C. to about 160° C. The pressures employed in the process of the present invention are those well known for, for example, in the range of about 1 to about 500 atmospheres and greater.

In a solution phase polymerization the alumoxane is preferably dissolved in a suitable solvent, typically in inert hydrocarbon solvent such as toluene, xylene, and the like in molar ratios of about $5\times10^{-3}$M. However greater or lesser amounts can be used.

The soluble metallocenes can be converted to supported heterogeneous catalyst by depositing said metallocenes on typical catalyst supports such as, for example, silica, alumina, and polyethylene. The solid catalyst in combination with an alumoxane can be usefully employed in slurry and gas phase olefin polymerizations.

After polymerization and deactivation of the catalyst, the product polymer can be recovered by processes well known in the art for removal of deactivated catalysts and solution. The solvents may be flashed off from the polymer solution and the polymer obtained extruded into water and cut into pellets or other suitable comminuted shapes. Pigments, antioxidants and other additives, as is known in the art, may be added to the polymer.

The polymer product obtained in accordance with this invention will have a weight average molecular weight in the range of about 1,400,000 to about 500 and preferably 500,000 to about 1000.

The polydispersities (molecular weight distribution) expressed as $\overline{Mw}/\overline{Mn}$ are typically from 1.5 to 4.0. The polymers contain 1.0 chain end unsaturation per molecule. Broadened MW can be obtained by employing two or more of the metal cyclopentadienyls in combination with the alumoxane as described in cofiled application entitled Process and Catalyst for Producing Polyethylene having a Broad Molecular Weight Distribution.

The polymers produced by the process of this present invention are capable of being fabricated into a wide variety of articles, as is known for homopolymers of ethylene and copolymers of ethylene and higher alpha-olefins. The present invention is illustrated by the following examples.

EXAMPLES

In the examples following the molecular weights were determined on a Water's Associates Model No. 150C GPC (Gel Permeation Chromatography). The measurements were made by dissolving polymer samples in hot trichlorobenzene (TCB) and filtered. The GPC runs were performed at 145° C. in TCB at 1.5 ml/min using two Shodex A80 M/S Gel columns of 9.4 mm internal diameter from Perkin Elmer Inc. 300 milliliter of 3.1 percent solutions in TCB were injected and the chromotagraphic runs monitored at sensitivity equal −64 and scale factor equal 65, The samples were run in duplicate. The integration parameters were obtained with a Water's Associates data module. An antioxidant, N-phenyl-2-naphthylamine, was added to all samples.

In the examples following the alumoxane was prepared in the following manner:

600 cc of a 14.5% solution of trimethylaluminum (TMA) in heptane was added in 30 cc increments at 5 minute intervals, with rapid stirring, to 200 cc toluene in a Zipperclave reactor under nitrogen and maintained at 100° C. Each increment was immediately followed by the addition of 0.3 cc water, The reactor was vented of methane after each addition. Upon completion of the addition, the reactor was stirred for 6 hours while maintaining the temperature at 100° C. The mixture, containing soluble alumoxane and a small quanity of insoluble alumina, is allowed to cool to room temperature and settle. The clear solution containing the soluble alumoxane is separated by decantation from the solids.

The molecular weights were determined by gel permeation chromatography at 145° C. on a Waters GPC 150C.

Example 1

A 1-liter stainless steel pressure vessel, equipped with an incline blade stirrer, an external water jacket for temperature control, a septum inlet and vent line, and a regulated supply of dry ethylene and nitrogen, was dried and deoxygenated with a nitrogen flow. 500 cc of dry, degassed toluene was introduced directly into the pressure vessel. 10.0 cc of 0.785 molar (in total aluminum) alumoxane was injected into the vessel by a gas tight syringe through the septum inlet and the mixture was stirred at 1,200 rpms and 80° C. for 5 minutes at 0 psig of nitrogen. 0.091 mg bis(cyclopentadienyl) zirconium dichloride dissolved in 2.0 ml of dry, distilled toluene was injected through the septum inlet into the vessel. After 1 minute, ethylene at 60 psig was admitted and while the reaction vessel was maintained at 80° C. The ethylene was passed into the vessel for 30 minutes at which time the reaction was stopped by rapidly venting and cooling. 13.6 gms of powdery white polyethylene having a $\overline{M}n$ of 39,500 and a $\overline{M}w$ of 140,000 with molecular weight distribution of 3.5.

Example 2

A 1-liter stainless steel pressure vessel, equipped with an incline blade stirrer, an external water jacket for temperature control, a septum inlet and vent line, and a regulated supply of dry ethylene and nitrogen, was dried and deoxygenated with a nitrogen flaw. 400 cc of dry, degassed toluene was introduced directly into the pressure vessel. 20.0 cc of alumoxane (0.785 mmoles in total aluminum) was injected into the vessel by a gas tight syringe through the septum inlet and the mixture was stirred at 1,200 rpms and 80° C. for 5 minutes at 0 psig of nitrogen. 0.2101 mg bis(methylcyclopentadienyl) zirconium dichloride dissolved in 2.0 ml of dry, distilled toluene was injected through the septum inlet into the vessel to give an Al/Zr ratio of $24 \times 10^3$. After 1 minute, ethylene at 60 psig was admitted for 30 minutes while maintaining the reaction vessel at 80° C. The reaction was stopped by rapidly venting and cooling. 28.6 gas of powdery white polyethylene having a $\overline{M}n$ of 55,900 and a $\overline{M}w$ of 212,000 with a molecular weight distribution of 3.8 and activity (Kg/gM.hr.atm) of 467.

Examples 3–5

Examples 3–5 were performed as Example 2 except that the metallocenes listed in Table 1 were substituted fort the metallocene in Example 2. The results of the examples are summarized in Table I.

Examples 6–8

Examples 6–8 were performed as Example 2 except that 0.2 mg of metallocenes as listed in Table 2 and 9.0 cc alumoxane were employed giving an Al/Zr of $8 \times 10^3$. The results are summarized in Table 2.

TABLE I

| Substituted Cyclopentadiene (Cp) Ligand Effects | | | | |
|---|---|---|---|---|
| Example | Catalyst[a] | $\overline{M}w$ | $\overline{M}n$ | MWD | Activity Kg/gM. hr.atm |
| 1 | Cp$_2$ZrCl$_2$ | 140,000 | 39,500 | 3.5 | 252 |
| 2 | (MeCp)$_2$ZrCl$_2$ | 212,000 | 55,900 | 3.8 | 467 |
| 3 | (EtCp)$_2$ZrCl$_2$ | 171,000 | 44,700 | 3.8 | 306 |
| 4 | (B-PP-Cp)$_2$ZrCl$_2$ | 282,000 | 78,200 | 3.6 | 335 |
| 5 | (Me$_5$CP)$_2$ZrCl$_2$ | 63,000 | 13,200 | 4.7 | 71 |

[a] Al/Zr = 24,000

TABLE II

| Example | Catalyst[a] | $\overline{M}w$ | $\overline{M}n$ | MWD | Activity Kg/gM. hr.atm |
|---|---|---|---|---|---|
| 6 | (Me$_5$Cp)$_2$ZrCl$_2$ | 47,300 | 13,200 | 3.6 | 142 |
| 7 | (MeCp)$_2$ZrCl$_2$ | 180,000 | 48,300 | 3.7 | 278 |
| 8 | (EtCp)$_2$ZrCl$_2$ | 184,000 | 50,000 | 3.7 | 281 |

[a] Al/Zr = 8,000

The physical properties of a polyethylene are largely determined by the polymer molecular weight and the polymer density. The previous examples have demonstrated that through the ligand effect, one can control the molecular weight of polyethylenes. The following examples demonstrated that through the same ligand effects, one can control the polymer density in copolymers such as ethylene copolymers. In addition, the control of polymer density in the following examples is demonstrated at fixed reaction conditions indicating that density control is mediated by ligand effects on the catalyst reactivity ratios.

Example 9

A 1-liter stainless steel pressure vessel, equipped with an incline blade stirrer, an external water jacket for temperature control, a septum inlet and vent line, and a regulated supply of dry ethylene and nitrogen, was dried and deoxygenated with a nitrogen flow. 400 cc of dry, degassed toluene was introduced directly into the pressure vessel. 10.0 cc of alumoxane solution (0.8 moles in total aluminum) was injected into the vessel by a gas tight syringe through the septum inlet and the mixture was stirred at 1,200 rpms and 50° C. for 5 minutes at 0 psig of nitrogen. 200 cc of liquid propylene at 25° C. was then added resulting in a pressure of 126.2 psig. 0.113 mg of bis(cyclopentadienyl)zirconium dimethyl in 10 ml of toluene was injected through the septum inlet into the vessel. Ethylene at 152.1 psig was admitted and the reaction vessel was maintained at 50° C. The ethylene was passed into the vessel for 30 minutes at which time the reaction was stopped by rapidly venting and cooling the reactor. 66.0 gms of copolymer having an intrinsic viscosity of 0.74 was isolated which contained 31 mole % propylene. The density was 0.854 g/cc at 23° C.

Example 10

A 1-liter stainless steel pressure vessel, equipped with an incline blade stirrer, and external water jacket for temperature control, a septum inlet and vent line, and a regulated supply of dry ethylene and nitrogen, was dried and deoxygenated with a nitrogen flow. 40 cc of dry, degassed toluene was introduced directly into the pressure vessel. 10.0 cc of alumoxane solution (0.8 moles in total alumina) was injected into the vessel by a gas tight syringe through the septum inlet and the mixture was stirred at 1,200 rpms and 50° C. for 5 minutes at 0 psig of nitrogen. 200 cc of liquid propylene at 25° C. was then added resulting in a pressure of 126.2 psig. 0.102 mg of dimethylsilyl-cyclopentadienyl zirconium chloride in 10 ml of toluene was injected through the septum inlet into the vessel. Ethylene at 152.4 psig was admitted and the reaction vessel was maintained at 50° C. The ethylene was passed into the vessel for 30 minutes at which time the reaction was stopped by rapidly venting and cooling the reactor. 12.0 gms of copolymer having an intrinsic viscosity of 0.52 was isolated which contained 43 mole % propylene. The density was 0.854 g/cc at 23° C.

Example 11

A 1-liter stainless steel pressure vessel, equipped with an incline blade stirrer, an external water jacket for temperature control, a septum inlet and vent line, and a regulated supply of dry ethylene and nitrogen, was dried and deoxygenated with a nitrogen flow. 400 cc of dry, degassed toluene was introduced directly into the pressure vessel. 10.0 cc of alumoxane solution (0.8 moles in total aluminum) was injected into the vessel by a gas tight syringe through the septum inlet and the mixture was stirred at 1,200 rpms and 50° C. for 5 minutes at 0 psig of nitrogen. 200 cc of liquid propylene at 25° C. was then added resulting in a pressure of 126.2 psig. 0.417 mg of bis(pentamethylcyclopentadienyl)zirconium dimethyl in 10 ml of toluene was injected through the septum inlet into the vessel. Ethylene at 151.5 psig was admitted and the reaction vessel was maintained at 50° C. The ethylene was passed into the vessel for 25 minutes at which time the reaction was stopped by rapidly venting and cooling the reactor. 30.5 gms of copolymer having an intrinsic viscosity of 0.81 was isolated which contained 3.6 mole % propylene. The density was 0.934 g/cc at 23° C.

The invention claimed is:

1. A process for polymerizing one or more olefins which comprises conducting the polymerization in the presence of the catalyst system comprising:

(a) a metallocene catalyst component represented by one of the formulas:

$(C_5R'_m)_p R''_s (C_5R'_m) MeQ_{3-p}$ and $R''_s (C_5R'_m)_2 MeQ'$ wherein Me is a Group 4B metal, $(C_5R'_m)$ is a di-alkyl, tri-alkyl, tetra-alkyl or penta-alkyl cyclopentadienyl or $(C_5R'_m)$ is a substituted cyclopentadienyl, each R', which can be the same or different, is hydrogen, an alkenyl, aryl, alkylaryl or arylalkyl radical having from 1 to 20 carbon atoms or two adjacent carbon atoms are joined together to form a $C_4$–$C_6$ ring, R" is a $C_1$–$C_4$ alkylene radical a dialkyl germanium or silicon, or an alkyl phosphine or amine radical substituting on and bridging two $(C_5R'_m)$ rings, each Q which can be the same or different is an aryl, alkyl, alkenyl, alkylaryl, or arylalkyl radical having from 1 to 20 carbon atoms or halogen, Q' is an alkylidene radical having from 1 to 20 carbon atoms, s is 0 or 1 and when s is 0, m is 5 and p is 0, 1 or 2 and when s is 1, m is 4 and p is 1; at least one R' is a hydrocarbyl radical when at least one Q is an alkyl radical; and (b) an alumoxane.

2. The process of claim 1 wherein the olefin is ethylene or an alpha olefin having from 3–18 carbon atoms.

3. The process of claim 1 wherein the olefin is ethylene.

4. A process for polymerizing one or more olefins which comprises conducting the polymerization in the presence of the catalyst system comprising:

(a) a metallocene catalyst component represented by one of the formulas:

$(C_5R'_m)_p R''_s (C_5R'_m) ZrQ_{3-p}$ and $R''_s (C_5R'_m)_2 ZrQ'$ wherein $(C_5R'_m)$ is a substituted cyclopentadienyl, each R', which can be the same or different, is hydrogen, an alkyl, alkenyl, aryl, alkylaryl or arylalkyl radical having from 1 to 20 carbon atoms or two adjacent carbon atoms are joined together to form a $C_4$–$C_6$ ring, R" is a $C_1$–$C_4$ alkylene radical, a dialkyl germanium or silicon, or an alkyl phosphine or amine radical substituting on and bridging two $(C_5R'_m)$ rings, each Q which can be the same or different is an aryl, alkyl, alkenyl, alkylaryl, or arylalkyl radical having from 1 to 20 carbon atoms or halogen, Q' is an alkylidene radical having from 1 to 20 carbon atoms, s is 0 or 1 and when s is 0, m is 5 and p is 0, 1 or 2 and when s is 1, m is 4 and p is 1; at least one R' is a hydrocarbyl radical when at least one Q is an alkyl radical; and (b) an alumoxane.

5. The process of claim 4 wherein the olefin is ethylene or an alpha olefin having from 3–18 carbon atoms.

6. The process of claim 4 wherein the olefin is ethylene.

7. A process for polymerizing one or more olefins which comprises conducting the polymerization in the presence of the catalyst system comprising:

(a) a metallocene catalyst component represented by one of the formulas:

$(C_5R'_m)_p R''_s (C_5R'_m) MeQ_{3-p}$ and $R''_s (C_5R'_m)_2 MeQ'$ wherein Me is a Group 4B, 5B, 6B metal, $(C_5R'_m)$ is a substituted cyclopentadienyl, each R', which can be the same or different, is hydrogen, an alkyl, alkenyl, aryl, alkylaryl or arylalkyl radical having from 1 to 20 carbon atoms or two adjacent carbon atoms are joined together to form a $C_4$–$C_6$ ring, R" is a $C_1$–$C_4$ alkylene radical, a dialkyl germanium or silicon, or an alkyl phosphine or amine radical substituting on and bridging two $(C_5R'_m)$ rings, each Q which can be the same or different is an aryl, alkyl, alkenyl, alkylaryl, or arylalkyl radical having from 1 to 20 carbon atoms or halogen, Q' is an alkylidene radical having from 1–20 carbon atoms, s is 1 and m is 4 and p is 1; at least one R' is a hydrocarbyl radical when at least one Q is an alkyl radical; and (b) an alumoxane.

8. The process of claim 7 wherein the olefin is ethylene or an alpha olefin having from 3–18 carbon atoms.

9. The process of claim 7 wherein the olefin is ethylene.

10. A process for polymerizing one or more olefins which comprises conducting the polymerization in the presence of the catalyst system comprising:

(a) a metallocene catalyst component represented by one of the formulas $(C_5R'_m)_p R''_s (C_5R'_m) MeQ_{3-p}$ and $R''_s (C_5R'_m)_2 MeQ'$ wherein Me is a Group 4B metal, $(C_5R'_m)$ is a substituted cyclopentadienyl, each R', which can be the same or different, is hydrogen, an alkyl, alkenyl, aryl, alkylaryl or arylalkyl radical having from i to 20 carbon atoms or two adjacent carbon atoms are joined together to form a $C_4$–$C_6$ ring, R" is a $C_1$–$C_4$ alkylene radical, a dialkyl germanium or silicon, or an alkyl phosphine or amine radical substituting on and bridging two $(C_5R'_m)$ rings, each Q which can be the same or different is an aryl, alkenyl, alkylaryl, or arylalkyl radical having from 1 to 20 carbon atoms or halogen, Q' is an alkylidene radical having from 1–20 carbon atoms, s is 0 or 1 and when s is 0, m is 5 and p is 0, 1 or 2 and when s is 1, m is 4 and p is 1; and (b) an alumoxane.

11. The process of claim 10 wherein the olefin is ethylene or an alpha olefin having from 3–18 carbon atoms.

12. The process of claim 10 wherein the olefin is ethylene.

* * * * *